April 4, 1972 W. FLEMER III Plant Pat. 3,092
SHADBLOW TREE
Filed Jan. 14, 1970
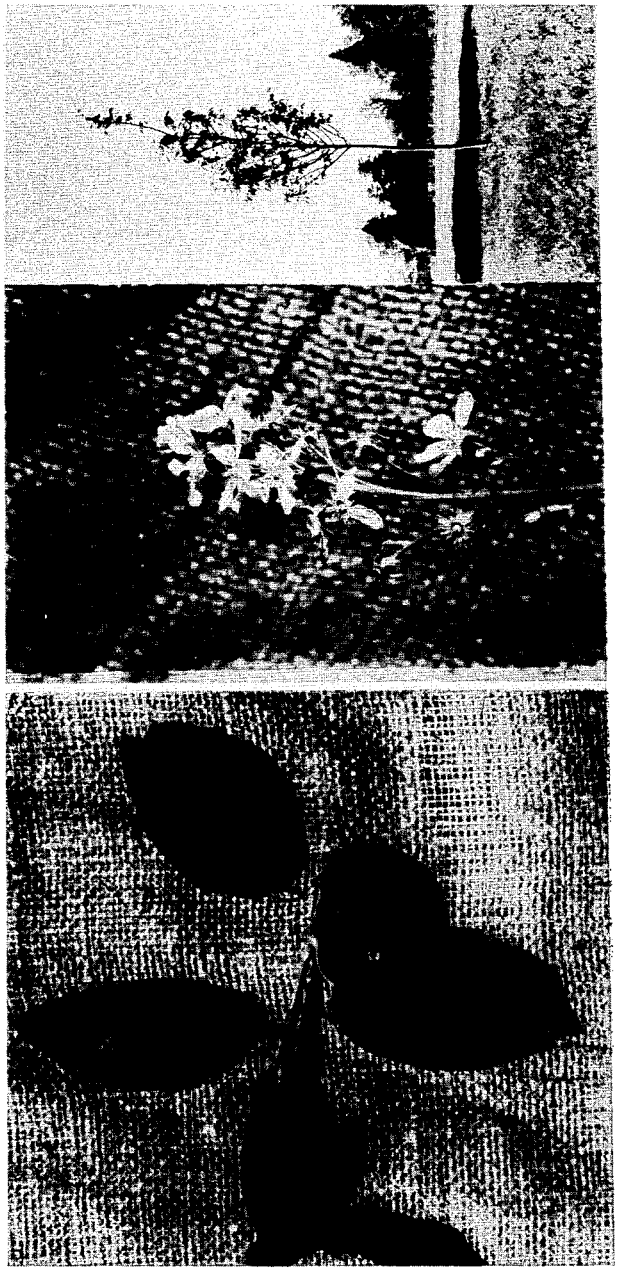
Inventor.
William Flemer, III
By: Robb & Robb
Attorneys.

United States Patent Office

Plant Pat. 3,092
Patented Apr. 4, 1972

3,092

SHADBLOW TREE

William Flemer III, Princeton, N.J., assignor to Treesearch, Kingston, N.J.

Filed Jan. 14, 1970, Ser. No. 2,979
Int. Cl. A01h *5/00*
U.S. Cl. Plt.—51 1 Claim

The present invention relates to a new and distinct variety of shadblow tree which was originated by me by crossing an unnamed and unpatented variety of the species botanically known as *Amelanchier laevis,* identified in my breeding records as #50–6, with an unnamed, unpatented and unidentified variety of the species botanically known as × *Amelanchier grandiflora,* which I acquired from Holand and which I believe was a seedling of Wyman's listed cross of *canadensis*×*laevis.*

The primary object of this breeding was to produce a new and improved variety of shadblow tree which is upright in form and free of "suckers" or new shoot sprouts which normally tend to grow from the roots and base of the plants of most of the ordinary seedling Amelanchiers. This objective was fully accomplished, along with other desirable improvements as evidenced by the following unique combination of characteristics which are outstanding in my new variety and which distinguish it from its parents, as well as from all other varieties of which I am aware:

(1) A vigorous, more rapid and upright habit of growth;
(2) Unusually hard and thick trunk and branches which are stronger and stiffer than those of other varieties of shadblow trees, with consequent greater resistance to extreme bending and damage by wind, snow and ice storms;
(3) Freedom from the production of base "suckers";
(4) Larger and broader flowers than those of either parent variety; and
(5) A distinctive and exceptionally attractive Fall foliage color varying from dark Red to strong Red and Dark Reddish Orange.

Asexual reproduction of my new variety by twig grafting, as performed by me in South Brunswick Township, N.J., shows that the foregoing characteristics and distinctions come true to form and are established and transmitted through succeeding propagations.

The accompanying drawing shows a typical tree specimen of my new variety, together with typical foilage and flower specimens on a larger scale.

The following is a detailed description of my new variety, with color terminology in accordance with the Munsell Color Chart, except where general color terms of ordinary dictionary significance are obvious:

Parentage: Seedling.
- *Seed parent.*—An unnamed variety of *Amelanchier laevis* identified as #50–6.
- *Pollen parent.*—An unnamed variety of *Amelanchier grandiflora.*

Propagation: Holds its distinguishing characteristics through succeeding propagations by twig grafting.

Locality where grown and observed: South Brunswick Township, N.J.

Tree: Small in relation to standard varieties of shade trees such as oaks, sycamores, tulip trees and the like which sometimes grow to over 100 feet tall; upright; tall in relation to other varieties of shadblow trees, and particularly in relation to the parent varieties; hardy.
- *Trunk.*—Slender; smooth. Color—Gray.
- *Branches.* — Slender; smooth. Color — Grayish Brown, Hue 7.5 YR 3/2. Lenticels—Moderately abundant.

Foliage:
- *Leaves.*—Thick. Quantity—Sparse. Size—Length—About 9 cm. Width—About 4½ cm. Shape—Oval-lanceolate. Color—Upper surface—Moderate Olive Green, Hue 2.5 GY 4/3. Under surface—Moderate Yellow Green, Hue 2.5 GY 5/5. Margin—Serrate; serrations about 1 mm. deep and about 2 mm. apart. Petiole—Medium length (about 2.5 cm. long). Glands—None. Stipules—Short; soon drop off.

Flower buds:
- *Hardiness.*—Very hardy.
- *Size.*—Length—About 1 cm. Width—About 0.3 cm.
- *Shape.*—Globular.
- *Color.*—White, but enclosed for their entire length in narrow green sepals.

Flowers:
- *Quantity.*—Abundant.
- *Size.*—Large; about 2.5 cm. in diameter.
- *Petalage.*—Number of petals 5. Shape of petals—Rounded. Size of petals—Length—About 1 cm. Width—About 0.7 cm. Color—White.

Fruits:
- *Borne.*—About June 20 to July 1.
- *Abundance.*—Abundant.
- *Shape.*—Globular.
- *Size.*—Length—About 0.9 cm. Width—about 1.2 cm.
- *Color.*—Dark Red Purple, Hue 2.5 R 3/7.

General observations: This new variety grows about one-third faster than normal seedling Amelanchiers grown under identical conditions in adjacent rows, and its strength and stiffness of trunk resist bending in ice storms when other ordinary seedlings bend over until their tops touch the ground. The upright form and non-suckering tree habit make the new variety especially suitable for street tree or other single trunk ornamental tree plantings.

I claim:

1. A new and distinct variety of shadblow tree, substantially as herein shown and described, characterized particularly as to novelty by the unique combination of a vigorous, more rapid and upright habit of growth, unusually hard and thick trunk and branches which are stronger and stiffer than those of other varieties of shadblow trees, with consequent greater resistance to extreme bending and damage by wind, snow and ice storms, freedom from the production of base "suckers," larger and broader flowers than those of either parent variety, and a distinctive and exceptionally attractive Fall foliage color varying from dark Red to strong Red and Dark Reddish Orange.

No references cited.

ROBERT E. BAGWILL, Primary Examiner